United States Patent [19]

Murphy et al.

[11] Patent Number: 5,242,902
[45] Date of Patent: Sep. 7, 1993

[54] DEFENSIN PEPTIDE COMPOSITIONS AND METHODS FOR THEIR USE

[75] Inventors: Christopher J. Murphy; Ted W. Reid, both of Davis; Mark J. Mannis, Carmichael; Bradley A. Foster, Davis; James S. Cullor, Woodland; Michael E. Selsted, Los Angeles; Robert I. Lehrer, Santa Monica; Tomas Ganz, Los Angeles, all of Calif.

[73] Assignee: The Regents of the University of California, Oakland, Calif.

[21] Appl. No.: 404,249

[22] Filed: Sep. 6, 1989

[51] Int. Cl.$^5$ .................... A61K 37/02; A61K 37/00; C07K 7/10
[52] U.S. Cl. ......................... 514/12; 435/1; 435/240.3; 514/13; 514/14; 514/887; 514/912; 514/914; 530/324; 930/190
[58] Field of Search .................... 514/12, 13, 14, 887, 514/912, 914; 530/324; 930/190

[56] References Cited

U.S. PATENT DOCUMENTS

| | | |
|---|---|---|
| 4,543,252 | 9/1985 | Lehrer et al. ................ 514/12 |
| 4,659,692 | 4/1987 | Lehrer et al. ................ 514/12 |
| 4,705,777 | 11/1987 | Lehrer et al. ................ 930/190 |
| 5,032,574 | 7/1991 | Wilde et al. ................ 530/324 |
| 5,032,575 | 7/1991 | Neufeld et al. ............... 514/12 |
| 5,034,375 | 7/1991 | Antoniades et al. ............ 514/12 |
| 5,045,531 | 9/1991 | Berkowitz et al. ............. 514/12 |
| 5,087,569 | 2/1992 | Gabay et al. ................. 514/12 |

FOREIGN PATENT DOCUMENTS 0190018 6/1986 European Pat. Off.
WO86/02271 4/1986 PCT Int'l Appl.

OTHER PUBLICATIONS

Kudryashov et al. (1990) Exp. Biol. & Med. 109:513-515.
Zhu et al. (1988) Proc. Natl. Acad. Sci. USA 85:592-596.
Singh et al. (1988) Biochem. Biophys. Res. Comm. 155:524-529.
Zhu et al. (1987) J. Steroid Biochem. 27:1017-1022.
Selsted et al. (1984) Infect. Immun. 45:150-154.
Zeya et al. (1966) Science 154:1049-1051.
Zeya et al. (1968) J. Exp. Med. 127: 927-941.
Zeya et al. (1971) Lab. Invest. 24:229-236.
Lehrer et al. (1977) J. Infect. Dis. 136: 96-99.
Lehrer et al. (1975) Infect. Immun. 11:1226-1234.
Lehrer et al. (1985) J. Virol. 54:467.
Selsted et al. (1985) Infect. Immun. 49:202-206.
Segal et al. (1985) J. Infect. Dis. 151:890-894.
Ganz et al. (1985) J. Clin. Invest. 76:1427-1435.
Wilde et al. (1989) J. Biol. Chem. 264:11200-11203.
Eisenhauer et al. (1989) Infec. Immun. 57:2021-2027.
Selsted et al. (1987) Infect. Immun. 55:2281-2286.
Murphy et al. (1989) Invest. Oph. Vis. Sci. Suppl. 30:149.
Mannis et al. (1989) Invest. Oph. Vis. Sci. Suppl. 30:363.

Primary Examiner—Ronald W. Griffin
Attorney, Agent, or Firm—Townsend and Townsend Khourie and Crew

[57] ABSTRACT

A method for treating cutaneous and corneal wounds as well as certain microbial-related diseases comprises topically applying a defensin peptide to the affected tissue. The compositions comprise a natural, synthetic, or analog defensin molecule having both a mitogenic activity capable of stimulating cell growth and an antimicrobial activity capable of inhibiting the growth of a wide variety of pathogens. In addition to therapeutic use, the defensins are useful as mitogens in cell and tissue culture media.

12 Claims, 6 Drawing Sheets

DEFENSIN PEPTIDE COMPOSITIONS AND METHODS FOR THEIR USE

BACKGROUND OF THE INVENTION

1. Field of the Invention

The present invention relates generally to methods and compositions for the enhancement of cellular proliferation and the treatment of wounds and other disorders. In particular, the invention relates to the use of defensin peptides for wound treatment and other applications.

Traumatic injury and disease can cause damage to the skin, tissue, and body organs which requires cellular regeneration for healing. Accidental injuries such as cuts, abrasions, burns, and intentional surgical procedures result in wounds which can affect large areas of the skin or affected body organs and can require lengthy periods to heal. Long healing times are a particular problem with wounds on sensitive areas, such as corneal wounds which are difficult to treat over prolonged periods. For these reasons, it would be desirable to provide methods and pharmacological agents which can be used to promote rapid healing of wounds and other injuries to the skin, tissue, and body organs.

A variety of cellular growth promoting hormones have been identified which can enhance cellular proliferation which have been used in wound treatment, including corneal wound treatment. Exemplary growth promoting hormones include epidermal growth factor, transforming growth factor $\beta$, insulin-like growth factor, platelet-derived growth factor, and the like. While use of these hormones continues to hold promise, no one growth promoting agent can be optimal for all situations. Moreover, it would be desirable to identify growth promoting agents which combine other desirable biologic activities, such as antimicrobial activity.

In addition to the wound itself, traumatic injury and surgical procedures present a substantial risk of microbial infection. While a wide variety of topical and systemic antimicrobial formulations are available, no one formulation is optimal for all circumstances. Moreover, it would be desirable to utilize antimicrobial compositions which possess additional desirable biological activities, such as the ability to promote cellular growth. It would also be desirable to identify antimicrobial compositions which are capable of inhibiting the growth of various resistant pathogens.

For the above reasons, it is an object of the present invention to provide pharmacological agents useful for the topical treatment of wounds and other disorders. Desirably, the compositions will be capable of providing a potent mitogenic activity which enhances the proliferation of epithelial cells, fibroblasts, and the like. The compositions will also be capable of inhibiting the growth of a wide variety of pathogenic and non-pathogenic microorganisms, including bacteria, viruses, and fungi. The compositions will be suitable for topical application to the skin and body organs, including the eye. Compositions will be suitable for incorporation into a wide variety of delivery vehicles.

2. Description of the Background Art

Defensins are a family of highly cross-linked, structurally homologous antimicrobial peptides found in the azurophil granules of polymorphonuclear leukocytes (PMN's) with homologous peptides being present in macrophages (Selsted et al., (1984) Infect. Immun. 45:150-154). Originally described as "Lysosomal Cationic peptides" in rabbit and guinea pig PMN Zeya et al., (1966), Science 154:1049-1051; Zeya et al., (1968), J. Exp. Med. 127:927-941; Zeya et al., (1971), Lab. Invest. 24:229-236; Selsted et al., (1984), supra.), this mixture was found to account for most of the microbicidal activity of the crude rabbit PMN extract against various microorganisms (Zeya et al., (1966), supra; Lehrer et al, (1977), J. Infect. Dis. 136:96-99; Lehrer et al., (1975), Infect. Immun. 11:1226-1234). Six rabbit neutrophil defensins have been individually purified and are designated NP-1, NP-2, NP-3A, NP-3B, NP-4, and NP-5. Their amino acid sequences were determined, and their broad spectra of activity were demonstrated against a number of bacteria (Selsted et al., (1984), Infect. Immun. 45:150-154), viruses (Lehrer et al., (1985), J. Virol. 54:467), and fungi (Selsted et al., (1985), Infect. Immun. 49:202-206; Segal et al., (1985), J. Infect. Dis. 151:890-894). Four peptides of the defensin family have been isolated from human PMN's and are designated HNP-1, HNP-2, HNP-3, and HNP-4 (Ganz et al., (1985), J. Clin. Invest. 76:1427-1435; Wilde et al. (1989) J. Biol. Chem. 264:11200-11203). The amino acid sequences of HNP-1, HNP-2, and HNP-3 differ from each other only in their amino terminal residues, while each of the human defensins are identical to the six rabbit peptides in 10 or 11 of their 29 to 30 residues. These are the same 10 or 11 residues that are shared by all six rabbit peptides. Human defensin peptides have been shown to share with the rabbit defensins a broad spectrum of antimicrobial activity against bacteria, fungi, and enveloped viruses (Ganz et al., (1985), supra.). Three defensins designated RatNP-1, RatNP-2, and RatNP-4, have been isolated from rat. Eisenhauer et al. (1989) Infection and Immunity 57:2021-2027. A guinea pig defensin (GPNP) has also been isolated, purified, sequenced and its broad spectrum antimicrobial properties verified (Selsted et al., (1987), Infect. Immun. 55:2281-2286). Eight of its 31 residues were among those invariant in six rabbit and three human defensin peptides. The sequence of GPNP also included three nonconservative substitutions in positions otherwise invariant in the human and rabbit peptides. Of the defensins tested in a quantitative assay HNP-1, RatNP-1, and rabbit NP-1 possess the most potent antimicrobial properties while NP-5 possesses the least amount of antimicrobial activity when tested against a panel of organisms in stationary growth phase (Selsted et al., (1984), Infect. Immun. 45:150-154; Ganz et al., (1985), J. Clin. Invest. 76:1427-1435). Defensin peptides are further described in U.S. Pat. Nos. 4,543,252; 4,659,692; and 4,705,777.

The use of growth factors in treating cutaneous and corneal wounds is described in European Patent Applications No. 190 019 and PCT Application No. WO 86/02271.

Work relating to the present invention was described in Murphy et al., (1989) Invest. Oph. Vis. Sci. Suppl., 30:149 and Mannis et al. (1989) Invest. Oph. Vis. Sci. Supp. 30:363.

SUMMARY OF THE INVENTION

According to the present invention, defensin compositions are administered to mammalian cells in order to enhance cellular proliferation and/or in inhibit the growth of pathogenic microorganisms. Surprisingly, defensin peptides have been found to possess a potent mitogenic activity capable of enhancing the growth of a variety of mammalian cells, including corneal, epithelial, lens epithelial cells, and fibroblasts, in addition to their previously-recognized antimicrobial activity. Usually, the defensin compositions will be applied topically to wounded skin or body organ where the defensin may act both as a wound healing promotant and an antimicrobial agent. Additionally, the defensin compositions of the present invention have been found to be particularly suitable for use as topical antimicrobial agents for a wide variety of pathogens, particularly for certain resistant strains of ocular pathogens responsible for diseases such as microbial keratitis and proliferative vitreoretinopathy. The defensin compositions will also be useful as growth promotants for mammalian tissue and cell culture media. For topical application, the defensins will typically be incorporated in a suitable carrier or base, such as ointment, cream, liquid, or the like.

DESCRIPTION OF THE SPECIFIC EMBODIMENTS

Figure 1:
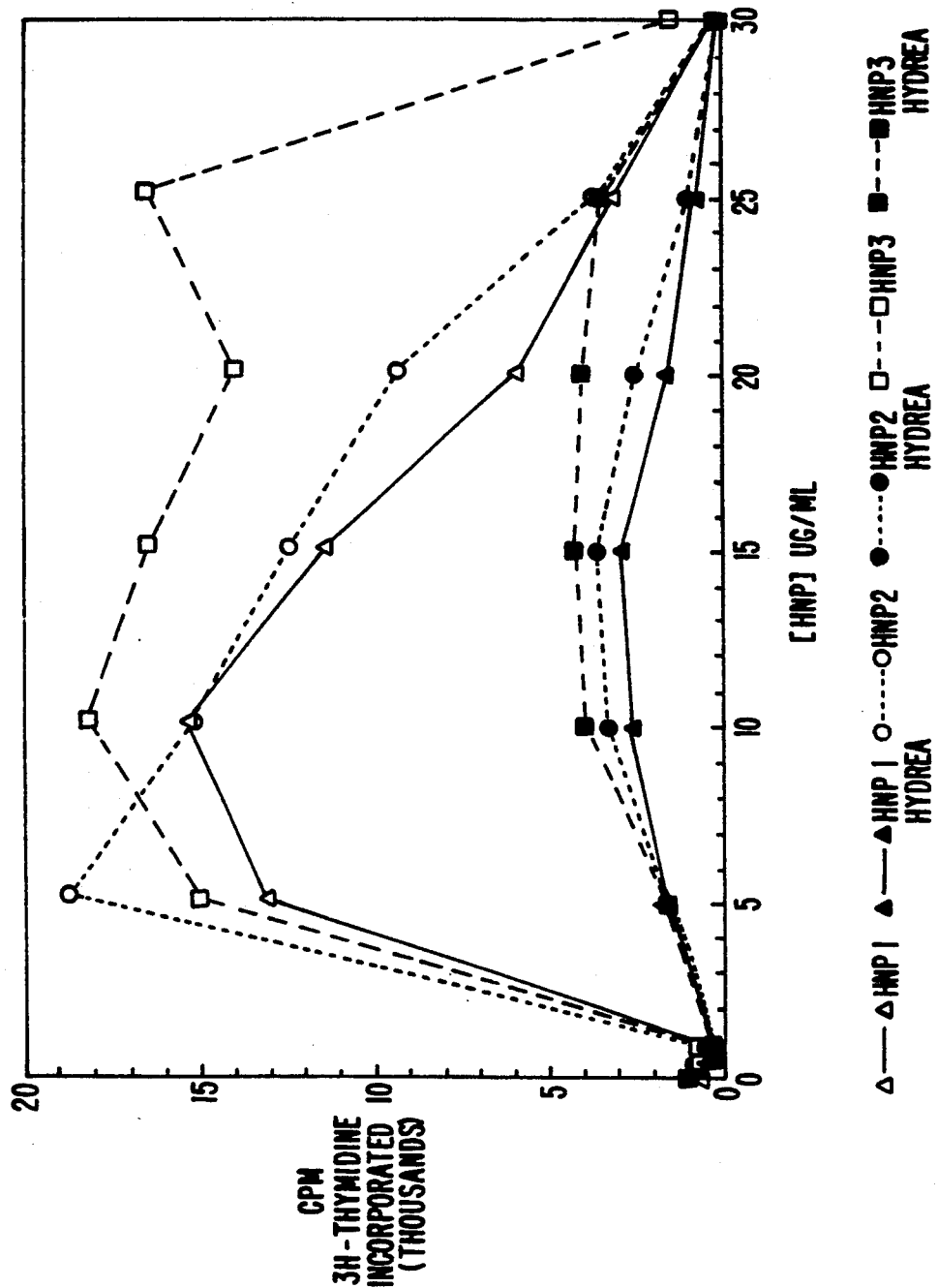
FIG. 1 is a graph demonstrating the mitogenic effect of human defensins on the growth of Nakano mouse lens epithelial cells, as described in detail in the Experimental section hereinafter.

Defensin peptides suitable for use in the methods and compositions of the present invention include natural defensin peptides isolated from known cellular sources, synthetic peptides produced by solid phase or recombinant DNA techniques, and defensin analogs which may be smaller peptides or other molecules having similar binding and biological activity as the natural defensin peptides.

The isolation and purification of natural defensin peptides are well described in the scientific and patent literature. In particular, such methods are described in the Experimental section hereinafter, as well as in U.S. Pat. Nos. 4,543,252; 4,659,692; and 4,705,777, the disclosures of which are incorporated herein by reference. The fourteen natural defensin peptides which have been identified to date are set forth in Table 1. It will be appreciated that additional natural defensin peptides may be identified in the future from either the species listed or other species, which peptides will likely be useful in the methods and compositions of the present invention.

TABLE 1

Amino Acid Sequences of
Human, Rabbit, Rat, and Guinea Pig Defensins
(Conserved residues are in bold and underlined.)

| | |
|---|---|
| HNP-1 | A CY CRIPA CIAG ERRY GT CIYQGRLWAF CC |
| HNP-2 | CY CRIPA CIAG ERRY GT CIYQGRLWAF CC |
| HNP-3 | D CY CRIPA CIAG ERRY GT CIYQGRLWAF CC |
| HNP-4 | V CS CRLVF CRRT EL RV GN CLIG GVSFTY CCTRV |
| NP-1 | VV CA CRRAL CLPR ERRA GF CRIR GRIHPL CCRR |
| NP-2 | VV CA CRRAL CLPL ERRA GF CRIR GRIHPL CCRR |
| NP-3A | GI CA CRRRF CPNS ERFS GY CRVN GARYVR CCSRR |
| NP-3B | GR CV CRKQLL CSYR ERRI GD CKIR GVRFPF CCPR |
| NP-4 | VS CT CRRFS CGFG ERAS GS CTVN GVRHTL CCRR |
| NP-5 | VF CT CRGFL CGSG ERAS GS CTIN GVRHTL CCRR |
| RatNP-1 | VT CY CRRTR CGFR ERLS GA CGYR GRIYRL CCR |
| RatNP-3 | CS CRYSS CRFG ERLS GA CRLN GRIYRL CC |
| RatNP-4 | A CY CRIGA CVSG ERLT GA CGLN GRIYRL CCR |

TABLE 1-continued
Amino Acid Sequences of
Human, Rabbit, Rat, and Guinea Pig Defensins
(Conserved residues are in bold and underlined.)

| GPNP | RRCICTTRTCRFPYRRLGTCIFQNRVYTFCC |
|---|---|

*leucine dipeptide

Code to abbreviations: A, alanine; C, cysteine; D, aspartic acid; E, glutamic acid; F, phenylalanine; G, glycine; H, histidine; I, isoleucine; K, lysine; L, leucine; N, asparagine; P, proline; Q, glutamine; R, arginine; S, serine; T, threonine; V, valine; W, tryptophan; Y, tyrosine Suitable synthetic peptides will usually comprise all or part of the amino acid sequence of a known peptide, more usually incorporating at least some of the conserved regions identified in Table 1. Usually, the synthetic peptides will incorporate at least one of the conserved regions, more usually incorporating two of the conserved regions, preferably conserving at least three of the conserved regions, and more preferably conserving four or more of the conserved regions. The synthetic peptides will usually be fifty amino acids or fewer, although there may be advantages in increasing the size of the peptide above that of the natural peptides in certain instances. The peptides will normally have a length in the range from about 10 to 50 amino acids, more usually being in the range from about 10 to 40 amino acids, and most typically being in the range from about 30 to 35 amino acids which corresponds generally to the length of the natural defensin peptides.

In some cases, it may be desirable to incorporate one or more non-natural amino acids in the synthetic defensin peptides of the present invention. Possible non-natural amino acids will usually have at least an N-terminus and a C-terminus and will have side chains that are either identical to or chemically modified or substituted from a natural amino acid counterpart. An example of a non-natural amino acid is an optical isomer of a naturally-occurring L-amino acid. Examples of chemical modifications or substitutions include hydroxylation or fluorination of C-H bonds within natural amino acids. Such techniques are used in the manufacture of drug analogs of biological compounds and are known to one of ordinary skill in the art.

Synthetic peptides having biological and binding activity the same or similar to that of natural defensin peptides may be produced by either of two general approaches. First, the polypeptides may be produced by the well-known Merrifield solid-phase chemical synthesis method wherein amino acids are sequentially added to a growing chain. See, Merrifield (1963) J. Am. Chem. Soc. 85:2149-2156. Systems for manually synthesizing peptides on polyethylene pegs are available from Cambridge Research Biochemicals, Cambridge, Mass. Automatic peptide synthesis equipment is available from several commercial suppliers, including Applied Biosystems, Inc., Foster City, Calif; Beckman Instruments, Inc., Waldwick, N.J.; and Biosearch, Inc., San Raphael, Calif. Using such automatic synthesizers according to manufacturer's instructions, peptides may be produced in gram quantities for use in the present invention.

Second, the synthetic defensin peptides of the present invention may be synthesized by recombinant techniques involving the expression in cultured cells of recombinant DNA molecules encoding a gene for a desired portion of a natural or analog defensin molecule. The gene encoding the defensin peptide may itself be natural or synthetic. Conveniently, polynucleotides may be synthesized by well known techniques based on the desired amino acid sequence. For example, short single-stranded DNA fragments may be prepared by the phosphoramidite method described by Beaucage et al. (1981) Tetra. Lett. 22:1859-1862. A double-stranded fragment may then be obtained either by synthesizing the complementary strand and annealing the strands together under appropriate conditions or by adding the complementary strand using DNA polymerase under appropriate conditions or by adding the complementary strand using DNA polymerase with an appropriate primer sequence. The natural or synthetic DNA fragments coding for the desired defensin peptide may then be incorporated in a suitable DNA construct capable of introduction to and expression in an in vitro cell culture.

The methods and compositions of the present invention may also employ synthetic non-peptide compositions that have biological activity functionally comparable to that of the known defensin peptides. By functionally comparable, it is meant that the shape, size, flexibility, and electronic configuration of the non-peptide molecule is such that the biological activity of the molecule is similar to the defensin peptides. In particular, the non-peptide molecules should display comparable mitogenic activity and/or antimicrobial activity, preferably possessing both activities. Such non-peptide molecules will typically be small molecules having a molecular weight in the range from about 100 to 1000 daltons. The use of such small molecules is frequently advantageous in the preparation of pharmacological compositions.

The identification of such nonpeptide analog molecules can be performed using techniques known in the art of drug design. Such techniques include, but are not limited to, self-consistent field (SCF) analysis, configuration interaction (CI) analysis, and normal mode dynamics computer analysis, all of which are well described in the scientific literature. See, e.g., Rein et al., *Computer-Assisted Modeling of Receptor-Ligand Interactions*, Alan Liss, N.Y., (1989). Preparation of the identified compounds will depend on the desired characteristics of the compounds and will involve standard chemical synthetic techniques. See, Cary et al. *Advanced Organic Chemistry*, part B, Plenum Press, New York (1983).

The compositions of the present invention comprise defensin polypeptides incorporated in a physiologically-acceptable carrier suitable for topical application to the affected area. The compositions may contain from about 0.1 nM to 10 mM defensin polypeptide, usually containing from about 0.01 μM to 1 mM defensin polypeptide, and more usually containing from about 0.1 μM to 100 μM defensin polypeptide. The nature of the carrier will vary depending on the intended area of application. For application to the skin, a cream or an ointment base is usually preferred, with suitable bases including lanolin, Silvadene TM (Marion) (particularly for the treatment of burns) Aquaphor TM (Duke Laboratories, South Norwalk, Conn.), and the like. It will also be possible to incorporate the defensin polypeptides in natural and synthetic bandages and other wound dressings to provide for continuous exposure of a wound to the peptide. Aerosol applicators may also find use. It is also possible that defensins will be incorporated in or coated on implanatable devices, such as heart pacemakers, intralumenal stents, and the like where both the antimicrobial and growth promoting activity would be of benefit. Coating may be achieved by nonspecific adsorption or covalent attachment.

For corneal treatment, the carrier will be suitable for application to the eyes. Preparation of suitable ophthalmic solutions requires careful consideration of factors such as isotonicity, the need for buffering agents, the need for preservatives, and sterilization. Lacrimal fluid is isotonic with blood, having an isotonicity value corresponding to that of an 0.9% sodium chloride solution. Ideally, an ophthalmic solution should have this isotonicity value, but eyes can tolerate isotonicity values as low as that of a 0.6% sodium chloride solution and as high as that of a 2.0% sodium chloride solution without substantial discomfort. Some ophthalmic solutions are necessarily hypertonic in order to enhance absorption and provide a concentration of the active peptide strong enough to exert a prompt and effective action. Suitable ophthalmic carriers include ointments, saline solutions, isotonic saline solutions, such as Sorbi-Care TM (Allergan Pharmaceuticals), Neodecadrone TM (Merck, Sharp, and Dhome) and the like. Suitable ointments bases sold under the tradename Lacrilube TM.

Other suitable ophthalmic vehicles include boric acid which has a pH slightly below 5.0. Phosphate buffer system may also be employed and adjusted for isotonicity may provide a choice of pH ranging from about 5.9 to 8.0. Pharmaceutical grade of methyl cellulose may also be employed having a variable viscosity.

Figure 2:
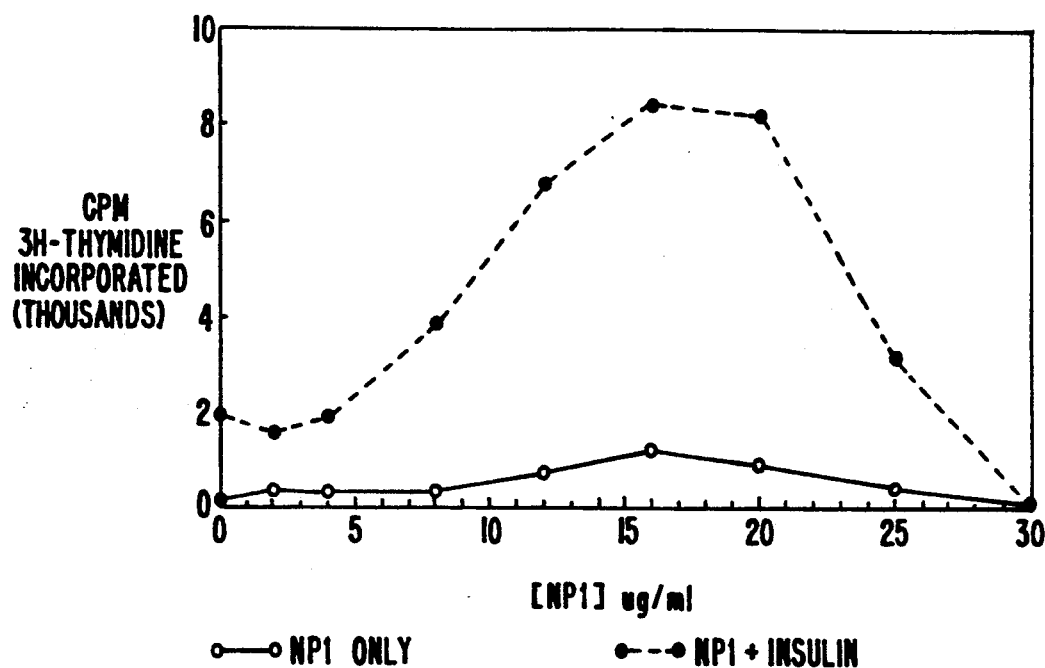
FIG. 2 is a graph illustrating the mitogenic effect of rabbit defensin on the growth of Nakano mouse lens epithelial cells in the presence and absence of insulin, as described in detail in the Experimental section hereinafter.

In addition to defensin peptides, the compositions of the present invention may include other known growth factors, such known growth factors, such as epidermal growth factor, platelet-derived growth factor, insulin-like growth factor, transforming growth factor, β, fibroblast growth factor, and the like. In certain cases, the presence of one or more additional growth factors may have a beneficial modulating potentiating effect on the activity of the defensin peptide as is shown in FIG. 2.

The defensin compositions of the present invention will be useful for treating a wide variety of wounds affecting virtually any tissues of the body. In particular, the compositions will be useful for treating cutaneous wounds affecting the epidermal and dermal layers of the skin, as well as injuries to the cornea and epithelial-lined hollow organs. The wounds may be caused by a wide variety of physical trauma, including cuts, abrasions, burns, chemical exposure, and the like, as well as from surgical procedures, such as surgical incisions and skin grafting. The wounds may also result from disease including chronic conditions, such as a venous stasis ulcers, diabetic ulcers, and other nonhealing (trophic) conditions.

The defensin compositions of the present invention will find particular use in treating corneal and scleral wounds, including wounds which affect the epithelial layer, stromal layer and endothelial layers of the eye. Heretofore, eye wounds have required particularly lengthy periods to heal and have been subject to numerous complications.

For use in wound treatment, the defensin compositions will usually have a concentration in the range described above. The defensin compositions will usually be applied to the affected area periodically, typically from about 4 to 12 times each day, usually over a period of from about 3 to 14 days, depending on the nature of the wound. In some cases, it may be desirable to apply the compositions indefinitely. The defensin compositions will find particular use in the treatment of wounds resulting from surgery and other intentional interventions where the compositions may be applied immediately after completion of the surgery.

In addition to the treatment of wounds, the defensin compositions of the present invention are particularly suitable for the treatment of microbial-related infections and diseases, particularly dermal infections, microbial-mediated dental disease, and ocular diseases such as microbial keratitis. For use in the treatment of such microbial infections, the compositions preferably employ a defensin concentration in the range set forth above. The compositions will typically be applied periodically, usually from about 2 to 12 times each day, for a period which may range from 3 to 21 days. For the treatment of dental disease, the compositions should be applied at least daily for an unlimited period.

The defensins of the present invention may find further use as cellular growth promoters in mammalian cell and tissue culture, particularly in the cell culture of epithelial cells and fibroblasts. The defensin peptides or analogs thereof will be introduced to the cell culture medium at a concentration of from about 1 nM to 10 mM, more usually at from about 0.1 μM to 100 μM. A wide variety of conventional growth medium may be employed.

The defensins will find particular use as a component in the solutions used for storage and transfer of corneas prior to transplant. The defensin concentration will be in the broad range set forth above. The defensins can act as both an antimicrobial and as a growth promotant after the cornea has been transplanted.

The following examples are offered by way of illustration, not by way of limitation.

EXPERIMENTAL

MATERIALS AND METHODS

1. Preparation

Human defensins (HNP-1, HNP-2, HNP-3) and rabbit defensins (NP-1 and NP-5) were isolated from neutrophils as described in Selsted et al. (1984), supra; and Ganz et al. (1985), supra. Human neutrophils were purified to 90% PMN.

2. In Vitro Cell Growth

Cell growth assays were performed as previously described in Reid et al., (1987), J. Biol. Chem. 262:229-233. Briefly, cells were grown to confluence in 96-well plates in media plus serum and arrested in G0/G1 by either serum starvation for 2-days (epithelial cells) or 8-10 day serum depletion followed by serum starvation for 1-day (fibroblasts). At this point the media was removed and new media with the desired factors was added. Approximately 16 hours later $^3$-thymidine was added and 20 to 28 hours later the cells were washed, lysed and the amount of $^3$H-thymidine incorporated into DNA was measured. In some cases, actual cell counts were performed.

3. In Vivo Epithelial Wound Healing

Capsaicin-treated corneas from adult rabbits were used to determine the effects of topically applied defensins on corneal re-epithelialization. Capsaicin depletes neuropeptides which have an effect on wound healing (data not shown). The rabbits received 0.4 ml of lidocaine diluted in 2.6 ml of sterile saline delivered subcutaneously between the cranial aspect of the interscapular space. After 10 minutes, 50 mg/kg of capsaicin (100 mg/ml) was delivered through a 1½ inch 25 gauge needle. Repeat injections of capsaicin was given once a day for four additional days. Three weeks from the last injection bilateral corneal defects were created as described below and the eyes treated topically with test solutions. The cornea was treated with two drops of test solution after creation of the epithelial defect. Upon completion of surgery, the rabbit was returned to its cage onto a warm heating pad. Sequential corneal photographs were taken after installation of fluoroscein and the rate of epithelial wound healing determined.

4. Bacterial Isolates

Corneal pathogenic isolates were obtained from equine and human patients with severe ulcerative keratitis. Human isolates were chosen for the clinical severity of the keratitis they produced. Equine isolates were obtained from a library of lyophilized pathogens and were selected for their relatively high resistance to commonly employed antibiotics as determined by minimum inhibitory concentrations. The panel of organisms was assembled in our laboratory and the growth characteristics for each organism was established by the following method.

A single colony of bacteria was inoculated into 40 ml trypicase soy broth (TSB) for eighteen hours. One milliliter (ml) of this culture was inoculated into four ml of fresh TSB, and harvested after four hours incubation at 37°C., or after the $A_{550}$ optical density had increased 10-fold. These log phase organisms were washed twice with 10 mM sodium phosphate buffer (pH 7.4, 2,000×G for 10 minutes), and adjusted to $1.0 \times 10^7$ colony forming units (CFU) per ml with reference to previously determined spectrophotometeric standards.

5. Bactericidal Assay Procedures

The antimicrobial activity of the defensins was tested against clinical isolates in the following manner: Isolates were grown in trypticase soy broth (TSB) and log phase organisms were harvested and suspended to a density of $1-2 \times 10^7$ CFU per milliliter. Defensins at concentrations ranging from 10 to 100 μg/ml were added to incubation mixtures containing $1-2 \times 10^6$ bacteria per milliliter. Sodium phosphate buffer, (10 mM, pH 7.4) was used as diluent for peptide and for the resuspension of bacterial cultures. Incubations were carried out at 37° C. in a saline water bath for up to 120 minutes. At timed intervals aliquots of the incubation mixtures were diluted 100 fold and plated in duplicate on trypticase soy agar plates. Surviving bacteria were enumerated by counting colonies after 24-48 hour incubation at 37° C.

In general, the bacteria under study were stable (with respect to colony counts) in 10 mM phosphate buffer for the duration of the incubations. However, alpha hemolytic Streptococcus exhibited a decrease in CFU's which was proportional to the time spent in the sodium phosphate buffer. To maintain viability of this organism, 2.0% TSB (v/v) and 3.0% (v/v) glucose was added to the incubation buffer. The addition (v/v) of 10.0% TSB +10.0% glucose to the buffer supported growth of alpha hemolytic Streptococcus and *Pseudomonas aeruginosa* and 2% TSB supported the growth of *Morganella morganii* in assays to assess the effect of target metabolism on killing by NP-5. A control sample containing only supplemented buffer was plated immediately after incubation and compared to the bacterial which had been in the supplemented buffer with defensin.

Bactericidal activity is expressed as the $\log_{10}$ of the initial colony count divided by the colony count at a specific time point, or as the $\log_{10} N_0/N$, where $N_0$ equals the initial CFU per milliliter, and N equals the CFU per milliliter after exposure to defensin. The larger numbers indicate increased antibacterial activity. Bacteriostatic activity is expressed as percent growth inhibition relative to the defensin-free control, or N-$N_0/N \times 100$.

RESULTS

1. In Vitro Stimulation of DNA Synthesis and Cell Division

The growth stimulatory properties of human defensins HNP-1, HNP-2, HNP-3 and rabbit defensins NP-1 and NP-5 in a serum free growth assay system were tested. SIRC rabbit corneal epithelial cells, Nakano mouse lens epithelial cells, and NIH 3T3 fibroblasts were utilized in these studies.

Figure 3:
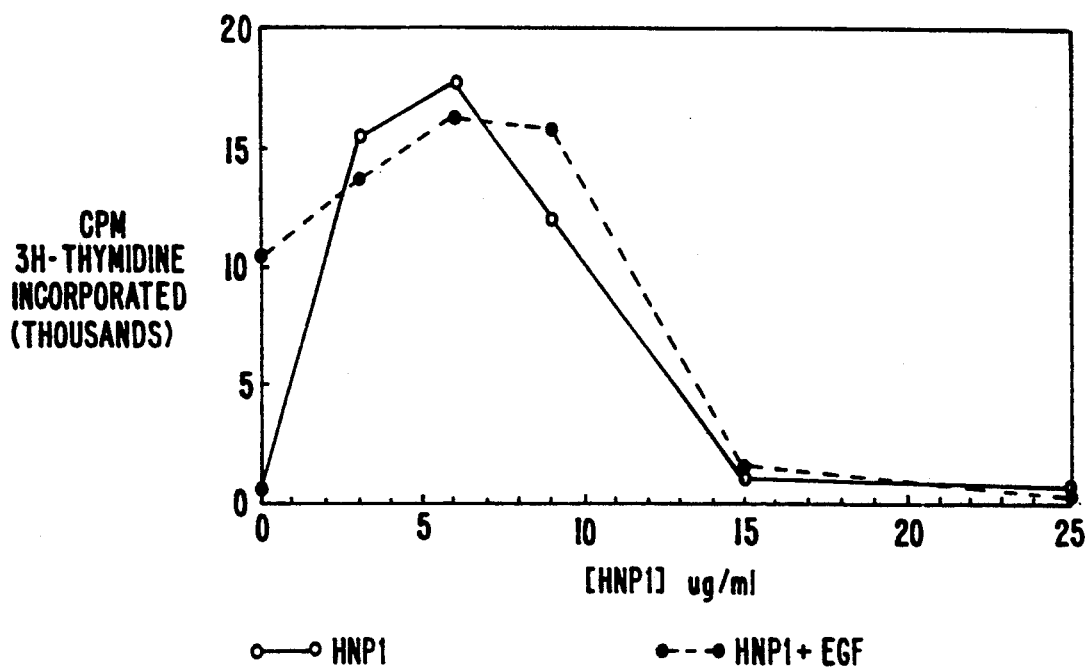
FIG. 3 is a graph illustrating the mitogenic effect of a human defensin on the growth of Nakano mouse lens epithelial cells in the presence and absence of epidermal growth factor, as described in detail in the Experimental section hereinafter.
Figure 4:
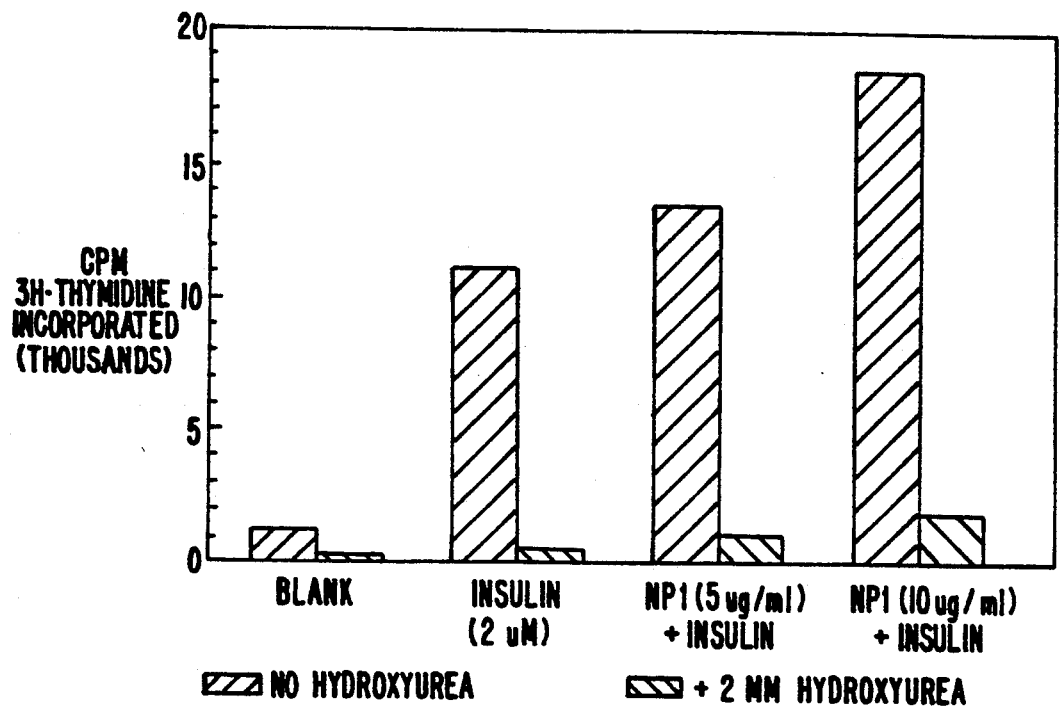
FIG. 4 is a chart illustrating the mitogenic effect of a rabbit defensin in combination with insulin on the growth of Nakano mouse lens epithelial cells in the presence and absence of hydroxyurea, as described in detail in the Experimental section hereinafter.
Figure 5:
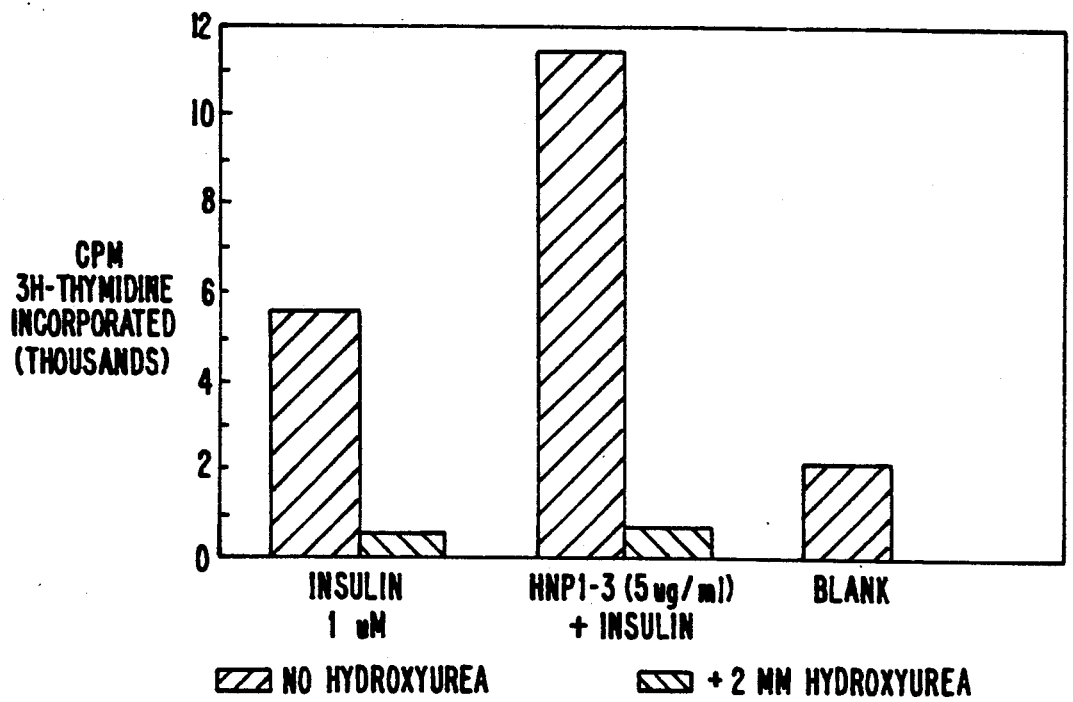
FIG. 5 is a chart illustrating the mitogenic effect of human defensins in combination with insulin on the growth of Nakano mouse lens epithelial cells in the presence and absence of hydroxyurea, as described in greater detail in the Experimental section hereinafter.
Figure 6:
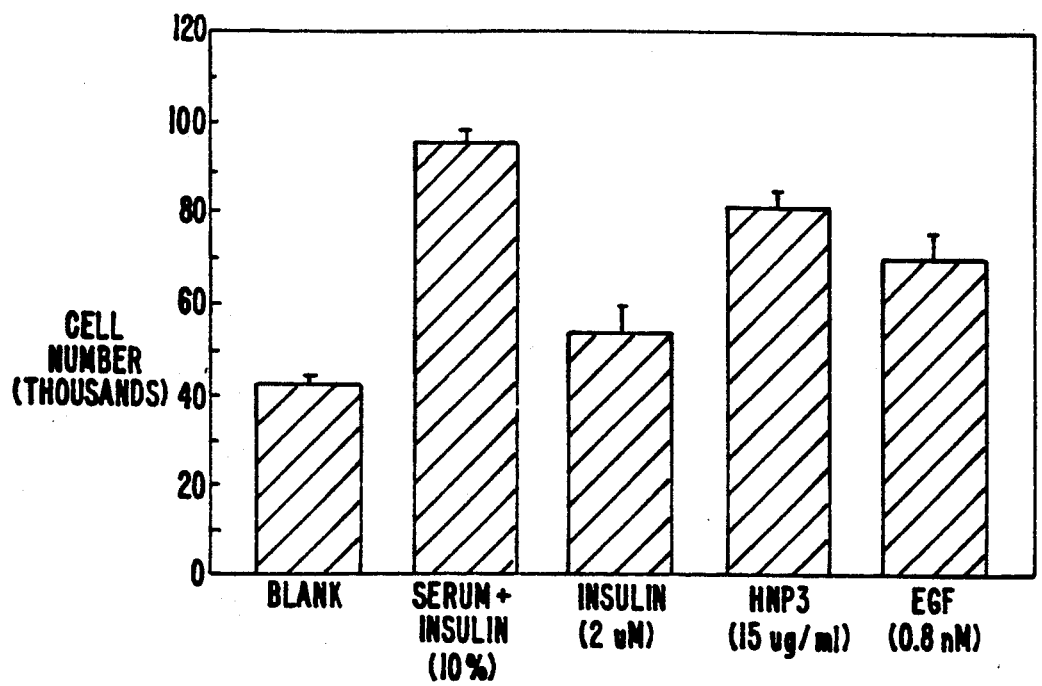
FIG. 6 is a chart comparing the mitogenic effect of insulin, a human defensin, and epidermal growth factor, on the growth of Nakano mouse lens epithelial cells, as described in greater detail in the Experimental section hereinafter.

Initial investigations with NP-1 and the human defensins demonstrated that defensins stimulate DNA synthesis in quiescent epithelial cells in a dose dependent fashion and resulted in suppression of DNA synthesis at higher concentrations (FIGS. 1 and 2). This effect was enhanced by insulin but not EGF (FIGS. 3 and 4). To determine whether defensins were causing an increase in scheduled DNA synthesis or by eliciting DNA repair the incubations were repeated with hydroxyurea. Hydroxyurea will suppress scheduled DNA synthesis but does not interfere with DNA repair. Results of these experiments conclusively show defensins to increase scheduled DNA synthesis (FIGS. 1, 4, and 5). Further evidence for the growth stimulatory properties of defensins was provided by experiments demonstrating an increase in actual cell number when incubated with defensin HNP-3 (FIG. 6). This stimulatory effect surpassed that of insulin and EGF which were tested at concentrations which elicit maximal response in our assay system employed.

Figure 7:
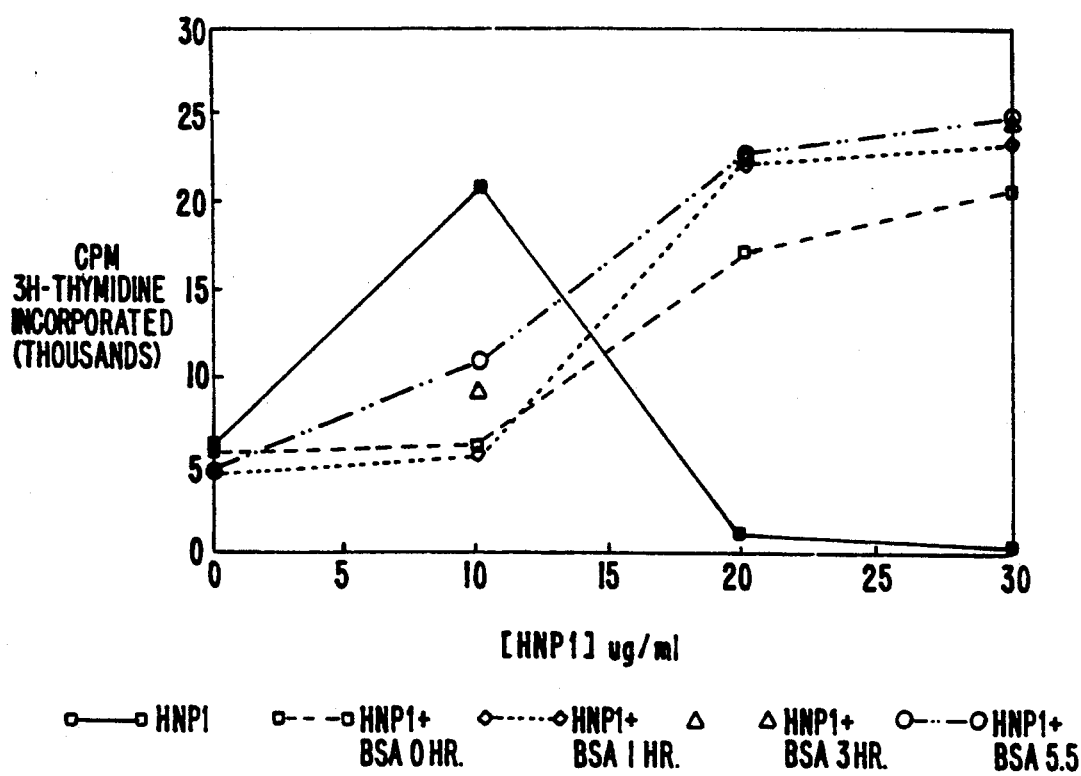
FIG. 7 is a graph illustrating the mitogenic effect of a human defensin on the growth of Nakano mouse lens epithelial cells as effected by the addition of bovine serum albumin, as described in greater detail in the Experimental section hereinafter.
Figure 8:
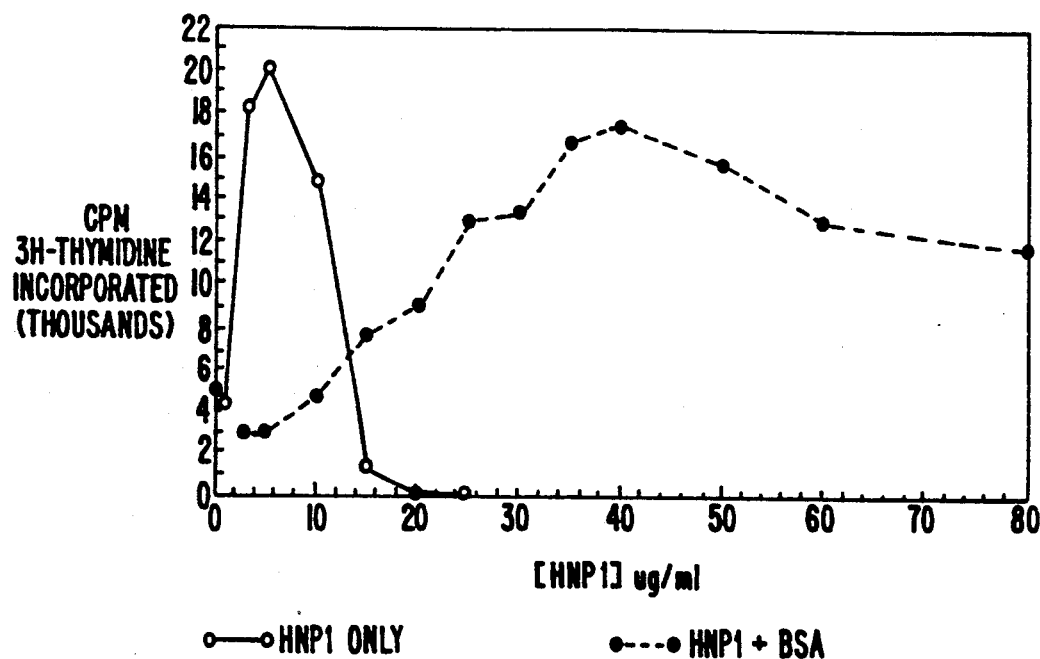
FIG. 8 is a graph illustrating the mitogenic effect of a human defensin on the growth of Nakano mouse lens epithelial cells in the presence and absence of bovine serum albumin, as described in greater detail in the Experimental section hereinafter.

Other experiments investigated the effects of adding 5 mg/ml bovine serum albumin (BSA) at varying times after stimulation by HNP-1 on the growth promoting properties of this defensin. This concentration was used for it is similar to tear albumin levels reported in the normal tear film. The results of these preliminary experiments (FIGS. 7 and 8) demonstrate that the response curve is shifted to the right and that the plateau phase is extended. Thus, these results show that defensins can retain their effectiveness in the presence of a major tear protein constituent.

Figure 9:
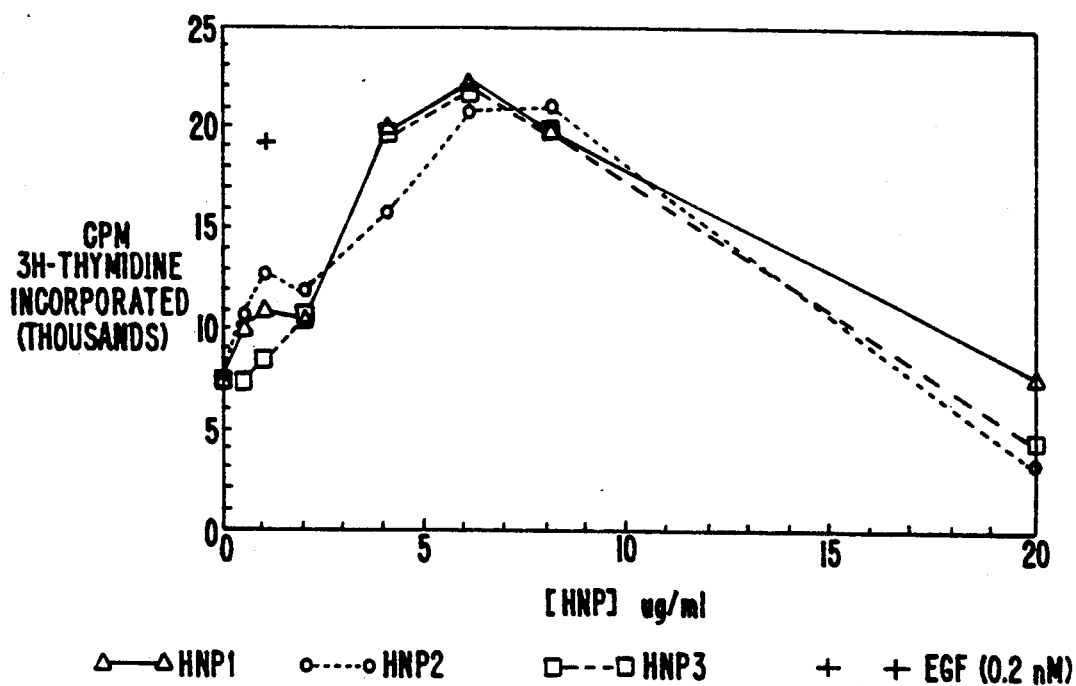
FIG. 9 is a graph comparing the mitogenic activity of three human defensins on the growth of rabbit corneal epithelial cells (SIRC), as described in greater detail in the Experimental section hereinafter.
Figure 10:
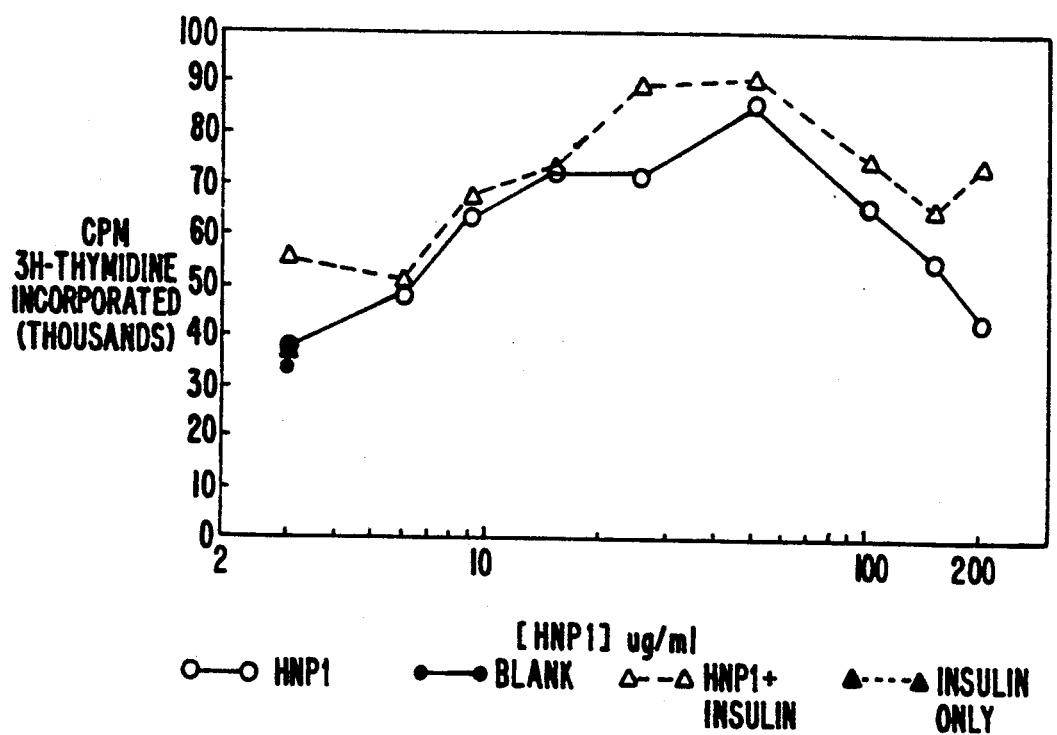
FIG. 10 is a graph illustrating the mitogenic effect of a human defensin on the growth of 3T3 fibroblast cells in the presence and absence of insulin, as described in greater detail in the Experimental section hereinafter.

The stimulatory properties of human defensin HNP-1 was further verified using corneal epithelial cells and 3T3 fibroblasts (FIGS. 9 and 10). The suppression observed at higher concentrations for both the corneal and lens epithelial cells was not observed for the 3T3 fibroblast cells.

Figure 11:
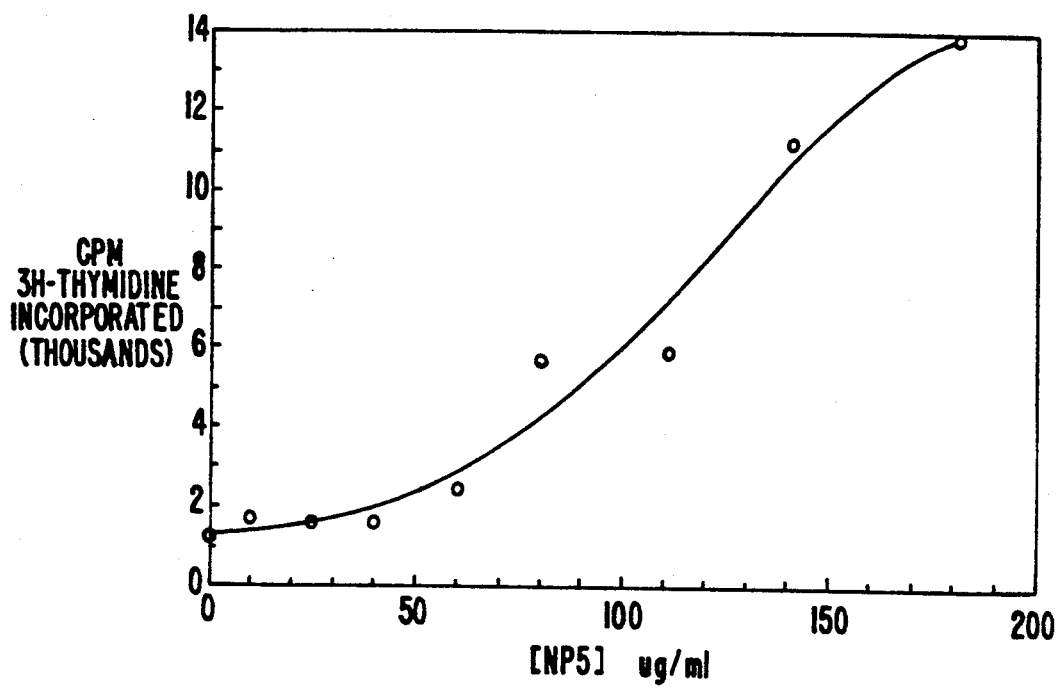
FIG. 11 is a graph illustrating the mitogenic effect of a rabbit defensin on the growth of Nakano mouse lens epithelial cells as a function of concentration, as described in greater detail in the Experimental section hereinafter.

The rabbit defensin NP-5, was also tested with lens epithelial cells and was found to be a strong stimulator of DNA synthesis (FIG. 11). In contrast to other defensins tested on epithelial cell lines, NP-5 remained stimulatory for cell synthesis at the highest concentrations investigated (180 μg/ml).

2. In Vivo Investigations of the Effect of Topical Human Defensin HNP-1 on Epithelial Wound Healing of the Neuropeptide Depleted Rabbit Cornea The effects of topically applied HNP-1 on the epithelial wound healing of neuropeptide depleted rabbit corneas was investigated. Corneas of rabbits treated systemically with capsaicin have impaired epithelial healing. In this model, capsaicin (50 mg/kg) was injected subcutaneously for 5 consecutive days into New Zealand white rabbits. Lidocaine was delivered subcutaneously into the capsaicin injection site 10 minutes prior to the first injection. Three weeks after the injections, the animals were anesthetized (ketamine/xylazine), topical anesthetic applied to the cornea, and the epithelium debrided circumferentially to the limbal margin of clear cornea. Absolute alcohol on microcellulose sponges and a dull #15 Bard Parker blade were used to remove the epithelium. Care was taken that no alcohol ran over the clear corneal edge to damage the limbal epithelium. The corneas were stained with fluorescein and photographed twice daily to monitor re-epithelialization. Systemic treatment with capsaicin, which limits elaboration of substance P and co-localized calcitonin gene related peptide, significantly delays re-epithelialization or the cornea when compared to noncapsaicin treated rabbits.

Two rabbits having capsaicin-treated corneas were treated with 100 μg/ml HNP-1 and two rabbits with 40 μg/ml of HNP-1 solubilized in sterile water. One eye of each rabbit was treated 4 times a day with the defensin solution with the fellow eye being treated with sterile water. Both corneas of each rabbit were stained with fluorescein twice a day and photographed with a camera twice daily to monitor re-epithelialization. A #47A wratten filter was placed over the camera flash to enhance visualization of epithelial defects.

Topically-applied defensin appeared to have no deleterious effect on the cornea or conjunctiva of the four experimental rabbits. In one rabbit both corneas re-epithelialized simultaneously (100 μg/ml). In two rabbits, the treated eye healed faster than the nontreated eye. In these rabbits, the one receiving 100 μg/ml defensin, re-epithialized at 5.5 days while the control eye healed at 6.5 days. The rabbit receiving 40 μg/ml defensin re-epithialized at 5 days while the control eye had not healed by the termination of the experiment at 12 days post wounding. In the final rabbit receiving 40 μg/ml defensin, neither cornea has healed by 12 days.

3. In Vitro Investigations of the Efficacy of Defensins Against Ocular Pathogens The antimicrobial propeties of the rabbit defensins NP-1 and NP-5 were tested against clinical isolates from corneas of humans and horses with microbial keratitis. Isolates tested from human corneas included *Staphylococcus aureus, Candida albicans, Pseudomonas aeruginosa, Morganella* and *Streptococcus pneumoniae.* Equine isolates tested were *Pseudomonas aeruginosa* and *Staphylococcus aureus.* The equine isolates were selected for their relative resistance to commonly employed antibiotics and their lack of clinical response to vigorous antimicrobial therapy.

Standard techniques were used to culture the clinical isolates, and their growth characteristics were established. Defensins were added at specific concentrations to a bacterial suspension containing 1-2 × 10$^7$ colony forming units (CFU) per ml incubated at 37° C. At timed intervals, aliquots of the incubation mixture were diluted 10-100 fold and plated in duplicate using the spiral plater. Surviving bacteria were enumerated by counting colonies after 24-48 hours of incubation. Bactericidal activity was expressed as a percentage of initial colony count, or as the $\log_{10} N_0/N$, where $N_0$ equals the initial colony count and N equals the colony count after exposure to defensin.

Substantial killing of all clinical isolates by NP-1 was observed at test concentrations ranging from 10.0 to 50.0 μg/ml (Tables 2 and 3). This natural antimicrobial molecule was quite effective in killing gram negative and gram positive ophthalmic as well as *Candida albicans*. There was no enhanced killing observed by extending the incubation period to 2 hours (data not shown). In comparison, NP-5 at test concentratios of 5 and 50 μg/ml produced little or no antimicrobial activity under the same assay conditions.

TABLE 2

Human Ocular Clinical Isolates

| Organism | NP-1 Concentration | Log Killing (vs. t = 0) 30 min. | 60 min. |
|---|---|---|---|
| *Candida albicans* | 10 μg/ml | >4 | >4 |
| α Streptococcus | 10 μg/ml | 1.6 | >4 |
| α Streptococcus | 50 μg/ml | 2.5 | >4 |
| α Streptococcus | 100 μg/ml | >4 | >4 |
| *Margonella* | 10 μg/ml | 1.5 | 2.2 |
| *Margonella* | 10 μg/ml | 1.7 | 2.9 |
| *Pseudomonas* | 10 μg/ml | 2.9 | >4 |
| *Streptococcus pneumoniae* | 10 μg/ml | >4 | >4 |
| *Streptococcus pneumoniae* | 100 μg/ml | >4 | >4 |

TABLE 3

Equine Ocular Pathogens (NP-1 at 10 μg/ml)

| Organism | Log Killing (vs. t = 0) 30 min. | 60 min. |
|---|---|---|
| *Pseudomonas aeruginosa* | >4 | >4 |
| *Pseudomonas aeruginosa* | >4 | >4 |
| *Pseudomonas aeruginosa* | >4 | >4 |
| *Staphylococcus aureus* | 2.4 | >4 |
| *Staphylococcus aureus* | >4 | >4 |

This study has demonstrated that rabbit defensin NP-1 possesses broad spectrum in vitro antimicrobial activity against human and equine ophthalmic clinical isolates at very low concentrations. This data coincides with investigations reported by Selsted et al. (1984) supra. where NP-1 and NP-5 were tested against human nonpathogenic bacterial isolates. In these investigations, NP-1 exhibited the greatest antimicrobial efficacy against gram-negative and gram-positive bacteria in stationary growth phase.

Although the foregoing invention has been described in detail for purposes of clarity of understanding, it will be obvious that certain modifications may be practiced within the scope of the appended claims.

What is claimed is:

1. A method for treating wounds in mammalian tissue to promote healing, said method comprising applying a defensin peptide to the wound in an amount sufficient to promote healing of the wound.

2. A method as in claim 1, wherein the defensin peptide is applied to a corneal epithelial wound.

3. A method as in claim 2, wherein the defensin peptide is applied to a corneal epithelial or stromal wound.

4. A method as in claim 2, wherein the defensin peptide is present in a physiologically-acceptable carrier at a concentration in the range from about 1 nM to 10 mM.

5. A method as in claim 2, wherein the defensin peptide is selected from the group consisting of HNP-1, HNP-2, HNP-3, HNP-4, NP-1, NP-2, NP-3A, NP-3B, NP-4, RatNP-1, RatNP-2, RatNP-4, and GPNP.

6. A method for treating corneal wounds and keratitis, said method comprising applying a defensin peptide to the eye of an affected host in an amount sufficient to effect said treating.

7. A method as in claim 6, wherein the host suffers from a traumatic wound to the eye.

8. A method as in claim 6, wherein the wound is a corneal epithelial wound.

9. A method as in claim 6, wherein the wound extends to the stromal layer.

10. A method as in claim 6, wherein the host suffers from microbial keratitis.

11. A method as in claim 6, wherein the defensin peptide is applied at a concentration of from about 1 nM to 10 mM.

12. A method as in claim 6, wherein the defensin peptide is selected from the group consisting of HNP-1, HNP-2, HNP-3, HNP-4, NP-1, NP-2, NP-3A, NP-4, NP-5, RatNP-1, RatNP-2, RatNP-4, and GPNP.

* * * * *